US 6,784,991 B2

(12) United States Patent
Rotter et al.

(10) Patent No.: US 6,784,991 B2
(45) Date of Patent: Aug. 31, 2004

(54) DIFFRACTIVE OPTICAL ELEMENTS AND GRID POLARIZERS IN FOCUSING SPECTROSCOPIC ELLIPSOMETERS

(75) Inventors: Lawrence D. Rotter, Pleasanton, CA (US); David Wang, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 80 days.

(21) Appl. No.: 10/172,904

(22) Filed: Jun. 17, 2002

(65) Prior Publication Data

US 2002/0191185 A1 Dec. 19, 2002

Related U.S. Application Data

(60) Provisional application No. 60/299,055, filed on Jun. 18, 2001.

(51) Int. Cl.[7] ............................................. G01N 21/21
(52) U.S. Cl. ...................................................... 356/369
(58) Field of Search ................................ 356/364–369, 356/630–632; 250/225

(56) References Cited

U.S. PATENT DOCUMENTS

| | | | | |
|---|---|---|---|---|
| 4,790,659 A | | 12/1988 | Erman et al. ................. | 356/369 |
| 5,333,052 A | * | 7/1994 | Finarov ....................... | 356/369 |
| 5,900,939 A | | 5/1999 | Aspnes et al. ............... | 356/369 |
| 5,946,098 A | | 8/1999 | Johs et al. ................... | 356/364 |
| 6,100,981 A | * | 8/2000 | Johs et al. ................... | 356/364 |
| 6,122,103 A | | 9/2000 | Perkins et al. .............. | 359/486 |
| 6,141,102 A | | 10/2000 | Johs et al. ................... | 356/364 |
| 6,375,870 B1 | | 4/2002 | Visovsky et al. ........... | 264/1.31 |
| 2002/0154319 A1 | * | 10/2002 | Yoshizawa et al. ......... | 356/630 |
| 2002/0159063 A1 | * | 10/2002 | Kanzaki ...................... | 356/369 |

FOREIGN PATENT DOCUMENTS

EP 0814467 A2 * 12/1997

OTHER PUBLICATIONS

M. Erman et al., "Spatially resolved ellipsometry," *J. Appl. Phys.*, vol. 60, No. 3, Aug. 1, 1986, pp. 859–873.
S. Liu et al., "Polarization device employing the combination effect of double refraction and diffraction," *Appl. Phys. Lett.*, vol. 67, No. 14, Oct. 2, 1995, pp. 1972–1974.
S. Liu et al., "Multilevel binary phase grating polarization device with a birefringent substrate," *Optics Letters*, vol. 20, No. 17, Sep. 1, 1995, pp. 1832–1834.
G.J. Sonek et al., "Ultraviolet grating polarizers," *J. Vac. Sci. Technol.*, vol. 19, No. 4, Nov./Dec. 1981, pp. 921–923.

* cited by examiner

Primary Examiner—Hoa Q. Pham
(74) Attorney, Agent, or Firm—Stallman & Pollock LLP

(57) ABSTRACT

One aspect of the present invention relates to a system and method for mitigating errors in SE data in order to determine changes in a polarization state of a source beam after interaction with a specimen. The system includes a light source for directing a source beam to a focusing optical element, a polarization system comprising a diffractive optical element or a wire grid polarizer, located between the focusing optical element and the specimen such that the source beam is polarized after being reflected from the focusing optical element. The polarized source beam is transmitted to the specimen. Changes in polarization state of the beam created by interaction with the sample are monitored to characterize the sample.

12 Claims, 6 Drawing Sheets

DIFFRACTIVE OPTICAL ELEMENTS AND GRID POLARIZERS IN FOCUSING SPECTROSCOPIC ELLIPSOMETERS

CROSS REFERENCE TO RELATED APPLICATION

This application claims the benefit of U.S. provisional application Serial No. 60/299,055 entitled "Diffractive Optical Elements and Grid Polarizers in Focusing Spectroscopic Ellipsometers" and filed on Jun. 18, 2001, the entirety of which is incorporated herein by reference.

TECHNICAL FIELD

The present invention relates to ellipsometry, wherein a beam with a known polarization state is focused on a sample and the change in polarization state after interaction with the sample is measured to determine characteristics of the sample. In particular, the present invention relates to systems and methodologies for mitigating errors induced in a focused beam spectroscopic ellipsometer employed in the evaluation of a samples such as semiconductor devices.

BACKGROUND ART

There is a need in the semiconductor as well as other industries to monitor compositional and geometrical features of a sample on a small scale. Various optical metrology tools have been developed to carry out this monitoring function including spectrophotometers and spectroscopic ellipsometers (SE).

Today, there is great interest in improving focused beam spectroscopic ellipsometers. In the semiconductor industry, measurements are typically made in the areas between devices on a wafer (streets). These streets are in effect wasted real estate on the wafer. As the capability improves to slice wafers, these streets are becoming smaller, necessitating even smaller focused beam spot sizes. In addition, there is current interest in measuring dimensional features such as critical dimensions in which a small focused spot is also desirable.

In a spectroscopic ellipsometer where the source beam is broadband, chromatic aberrations in the focusing optical elements limits the minimum achievable source spot size on the specimen. A larger spot size reduces the amount of light transported to the detector by the collection optics thus reducing throughput. Therefore, efforts are made to design systems with minimal chromatic aberration. If a refractive lens system is used to focus the beam, care must be taken to select the correct materials, curvatures and lens spacing to reduce chromatic aberrations. Another approach to reducing chromatic aberrations is to use curved mirrors to focus the beam.

In most commercial systems, the probe beam in an SE is polarized prior to being focused by either the refractive or reflective elements. However, if the source beam is polarized prior to being focused, polarization errors can be introduced. For example, the reflection from a focusing mirror can alter the polarization state of the source beam. When focusing a source beam with a lens or lens assembly, the birefringence in the lens materials tends to destabilize the polarization state. For example, a temperature change can adversely affect the polarization state of a polarized source beam before the beam is passed to the specimen. These effects introduce complications and sources of error into the analysis of the SE data.

This problem can be avoided by polarizing the source beam after it has been focused. Prior art attempts to achieve this result have included the use of a prism polarizer or a dichroic sheet polarizer. Unfortunately, dichroic sheet polarizers operate in only a limited spectral range. This is because dichroic sheet polarizers are polymer based. The polymers absorb ultraviolet, mid- and far- infrared radiation, which limits their use in the visible and near-infrared wavelengths. Prism polarizers are also problematic because they induce spherical aberration and chromatic aberration in a focused beam. This is not particular to prism polarizers, as aberrations may occur in any slab of material. Generally, as the thickness of the slab increases, the amount or severity of aberrations increases as well. However, because prism polarizers are relatively thick, the degree of aberrations formed is particularly more severe.

Therefore, it is desirable to accurately characterize a specimen without incurring such complications and sources of error by suitably polarizing the beam after focusing.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides a novel optical measurement system and a methodology for mitigating and/or eliminating errors introduced into SE data that can be caused by a change in the polarization state of a polarized source beam focused by a mirror or lens. More specifically, the present invention involves polarizing the source beam after it has been focused in order to prevent or mitigate undesirable modifications to the polarization state of the polarized source beam. In addition, this specific approach reduces aberrations induced by polarizing a source beam after it has been focused. As a result, more light reaches the detector, thereby increasing the system throughput.

These results are accomplished in part by using a novel polarization system that is located between a focusing optical element and the specimen such that a source beam of light is polarized only after being focused. In particular, the polarization system may include at least one of a diffractive optical element and a wire grid polarizer in order to effectively polarize the source beam before being passed to the specimen. By way of example, the diffractive optical element may be used alone and/or added to one or more surfaces of a prism polarizer in order to compensate for aberrations introduced into the focused source beam by the prism polarizer. In addition, the polarization system may include a plurality of diffractive optical elements and/or wire grid polarizers such that the plurality of elements and/or grid polarizers is arranged in a sequence.

One aspect of the present invention relates to an optical measurement system that contains an SE measurement device. The system includes a light source, a polarization system, and a light detection system. The light source directs a source beam of light to a focusing optical element. Examples of the focusing optical elements include a focusing mirror and a focusing lens (e.g., lens assembly). The source beam is then polarized before reaching the specimen. Polarization of the source beam is performed by a polarization system, which is located between the focusing optical element and the specimen. After the source beam contacts the specimen and reflects therefrom, it is transmitted to the light detection system. The detection system determines the changes in polarization state of the source beam resulting from the interaction with the specimen.

Another aspect of the present invention relates to a polarization system employed within a SE. The polarization system contains one or more diffractive optical elements that are designed such that one polarization state has maximum diffraction efficiency in one order while the orthogonal polarization state has maximum efficiency in a different order. Therefore, the two orthogonal polarization states are separated into two beams that are focused to different locations on the specimen. Such an arrangement permits the use of spatial filtering (e.g., at the entrance aperture of the spectrometer) in order to transmit only the desired polarization state from the specimen to the detector. The polarization efficiency can be further increased by generating a phase grating on a birefringent substrate. Alternatively, or in addition, two such diffractive optical elements can be assembled to form a micro-array of Rochon prisms.

According to yet another aspect of the present invention, the polarization system may comprise a prism polarizer coupled to the diffractive optical element such that one or more diffractive elements may be added to one or more surfaces of a prism polarizer. The diffractive optical element configured in this manner compensates for aberrations induced by the prism polarizer.

More information on diffractive optical elements can be found in: "Achromatic birefringent grating polarizer," S. Q. Liu, Y. S. Chen, R. X. Wang, Journal of modern optics. FEB 01, 1998 v 45 n 2335; "Polarization device employing the combination effect of double refraction and diffraction," Shangqing Liu, Chengxiang Li and Yangsong Chen, Appl. Phys. Lett. 67 (1995) 1972; and "Multilevel binary phase grating polarization device with a birefringent substrate," Shangqing Liu and Yansong Chen, Opt. Lett. 20 (1995) 1832.

Yet another aspect of the present invention relates to a polarization system used in a SE measurement device wherein the polarization system contains a wire grid polarizer. The wire grid polarizer can act as a broadband dichroic sheet polarizer in the focused beam of the SE. Employing a wire grid polarizer allows one linear polarization state to be transmitted while the orthogonal polarization state can be either reflected or absorbed. This is accomplished in part by having a grid spacing smaller than the wavelength of the incident light (source beam). In addition, the effective medium combination of wire and adjacent areas may be linearly dichroic. Therefore, only a single linear polarization state is transmitted to the specimen.

Furthermore, the material of the wire grid substrate has a high transmittance in the spectral range that is to be detected. For example, suitable wire grid substrate materials have minimal imaginary parts of a dielectric response over the widest spectral ranges possible. In particular, for vacuum ultraviolet to infrared operation, suitable materials include calcium fluoride ($CaF_2$), magnesium fluoride (MgF), aluminum oxide ($Al_2O_3$), lithium fluoride (LiF) and barium fluoride (BaF2). Suitable wire grid materials include, silver (Ag), gold (Au), aluminum (Al) and the like and other such materials that have maximal conductivity over the widest spectral ranges possible.

Still yet another aspect of the present invention relates to a polarization system employed within a measurement device such as a SE, wherein the polarization system includes a combination of a diffractive optical element and a wire grid polarizer.

Still yet another aspect of the present invention relates to a method for mitigating aberrations and distortions with respect to a focused source beam of an SE. The method involves directing a source beam of broadband light to a focusing optical element to focus the source beam. The focused source beam can be polarized by a polarization system. Subsequently, the polarized source beam is transmitted to a specimen. The source beam may include a plurality of wavelengths such as deep ultraviolet, infrared, and visible light. The focusing element may be a focusing mirror, lens, and/or lens assembly, depending on the desired application.

Moreover, mitigating the occurrence of aberrations introduced into the focused source beam facilitates obtaining a minimal source spot size on a specimen. As a result, one obtains simultaneously a single, well-defined polarization state of the source beam and a small source beam spot at the specimen, thereby facilitating evaluation and characterization of film properties of a semiconductor device.

DISCLOSURE OF INVENTION

Figure 1:
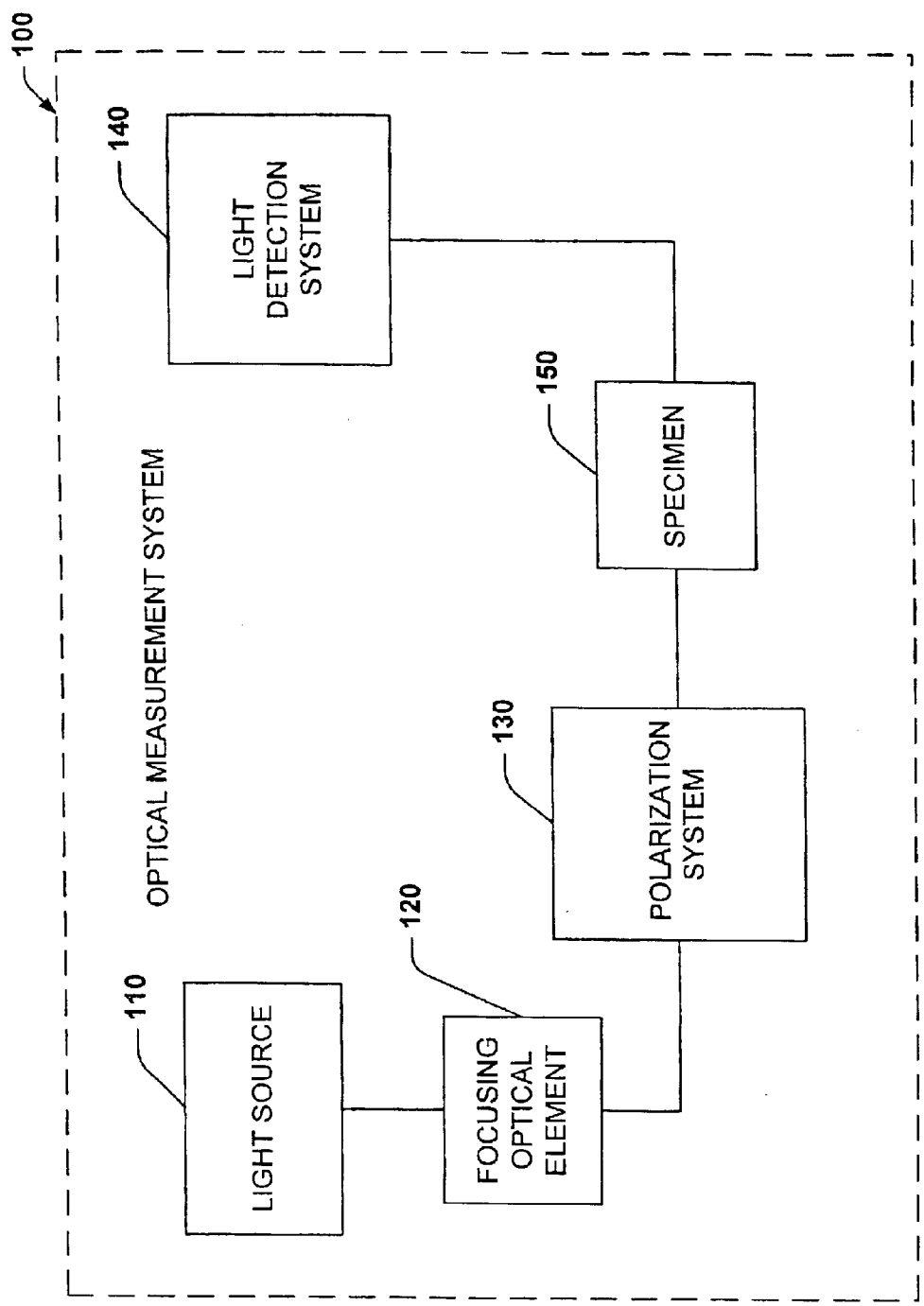
FIG. 1 illustrates a high-level, schematic block diagram of an optical measurement system in accordance with one aspect of the present invention.

The present invention involves a system and method for mitigating complications and errors that are introduced into the analysis of SE data generated by a focused probe beam. This is accomplished in part by employing a novel polarization system that polarizes the source beam after it has been focused. Polarizing the source beam after it has been focused stabilizes the polarization state to eliminate a change in the polarization state. In addition, the occurrence of chromatic aberrations on a source spot of a specimen are reduced. Thus, throughput in the beam of light is maximized in order to effectively evaluate the specimen.

Furthermore, polarizing after refractive optics (e.g., lens, lens assembly) may be used to eliminate polarization state changes induced by birefringence in the lens material. This may be stress birefringence in nominally isotropic materials or intrinsic birefringence in anisotropic materials. With respect to isotropic materials, polarizing after the lens increases the uniformity across a wavefront of the polarization state, because stress birefringence tends to be spatially non-uniform. It also permits the use of lower cost grades of lens material, which tend to have more stress birefringence.

With respect to anisotropic materials, polarizing after the focusing lens permits the use of lens materials with intrinsic birefringence without requiring extraordinary alignment of the birefringence axis that would otherwise be necessary to prevent the lens from inducing substantial changes in the polarization state. This increased freedom of choice of lens materials is particularly important in the vacuum ultraviolet where there is a limited choice of transparent materials and some of them, notably $Al_2O_3$ and $MgF_2$, are birefringent. $Al_2O_3$ is particularly important for achromatizing lenses in the vacuum ultraviolet.

According to one aspect of the present invention, the polarization system includes at least one of a diffractive optical element and a wire grid polarizer. According to another aspect of the present invention, the polarization system includes a diffractive optical element coupled to a prism polarizer such that one or more diffractive optical elements are added to one or more surfaces of the prism polarizer in order to compensate for chromatic and/or spherical aberrations introduced into the focused source beam by the prism polarizer. In addition, a plurality of diffractive optical elements may be included in the polarization system and arranged in a sequence in order to increase the degree of polarization and/or stabilization of the polarization state of the source beam.

The diffractive optical element, when employed either alone or with other polarizers (e.g., prism polarizer), is relatively thin compared to a conventional prism polarizer. The prism polarizer is typically thick when compared to either the diffractive optical element or to a thickness that is necessary for the wire grid polarizer which is suitable to carry out the present invention.

Furthermore, the diffractive optical element can be used as a broadband polarizer and designed such that one polarization state has maximum diffraction efficiency in one order, such as zeroth order, while the orthogonal polarization state has maximum efficiency in a different order. Therefore, the two orthogonal polarization states are separated into two beams. The two beams are focused to different locations on a specimen, thereby permitting the use of spatial filtering to transmit only the desired polarization state to the detector. Furthermore, the polarization efficiency may be increased, for example, by generating a phase grating on a birefringent substrate of the diffractive optical element. Alternatively, or in addition, two diffractive optical elements can be arranged to form a micro-array of Rochon prisms.

According to another aspect of the present invention, the polarization system may contain a wire grid polarizer, either alone or in combination with a diffractive optical element. In addition, the polarization system may include a plurality of wire grid polarizers which can be arranged in a sequence. Employing a sequence of wire grid polarizers in the focused source beam may increase the degree of polarization and/or stabilization of the polarization state of the source beam.

The wire grid polarizer can be employed as a dichroic sheet polarizer such that one linear polarization state is transmitted to the specimen, while the orthogonal polarization state is either reflected or absorbed. This can be accomplished in part by using a grid spacing smaller than the wavelength of the source beam.

Furthermore, the substrate material of the diffractive optical element and/or wire grid polarizer may be selectively chosen in order to decrease the amount of aberrations introduced into the source beam. In particular, a substrate having a surface shape which is less likely to create or lead to the formation of aberrations may further improve the throughput in the collection source beam. Alternatively, any substrate material may be chosen for the specimen with the ensuing aberrations corrected by a binary phase grating positioned on one or more of the substrate surfaces.

The present invention may be further described with respect to schematic diagrams of various SE systems in accordance with the present invention as illustrated in FIGS. 1–6 below.

Referring to FIG. 1, a high-level schematic diagram of an optical measurement system 100 according to one aspect of the present invention is shown. The optical measurement system 100 comprises a light source 110, a focusing optical element 120, a polarization system 130 and a light detection and processing system 140. The light source 110 may provide a source beam of broadband light in a wide spectral range of wavelengths, such as ultraviolet, infrared, and visible light, depending on the desired application. Broadband light includes wavelengths from about 140 nm to about 900 nm.

The light source 110 directs the source beam to the focusing optical element 120. An example of the focusing optical element 120 is a focusing mirror which provides a high level of achromaticity to the source beam and thus is desirable to use in a SE in order to achieve the smallest source spot size on a specimen 150 with respect to a broadband source beam. In addition, a focusing lens or lens assembly may be used as the focusing optical element 120. In commercial systems, it necessary to measured spots sizes of less than about 50 microns in diameter and there is a need to reduce that spot size to about 25 microns in diameter.

In accordance with the subject invention, the source beam in the present invention is polarized by the polarization system 130 after it is has been focused. This mitigates complications and analysis errors arising from polarizing the source beam before it is focused. Such complications and analysis errors are due to undesirable modifications of the polarization state of the source beam.

Different polarization systems may be employed in order to polarize the source beam in definite polarization states. As described in more detail later, the polarization system that is applied to the source beam after it has been focused stabilizes the polarization state of the source beam in order to obtain more accurate data. Polarization at this stage of the optical measurement system may also facilitate achieving a minimal source spot size on the specimen which is desirable in order to achieve higher throughput.

Once the source beam has been polarized and transmitted to the specimen 150, the reflected polarized source beam is passed onto a number of components within the light detection system 140. The detection system 140 facilitates determining a change in the polarization state of the source beam due to the interaction with the sample. The detection system 140 comprises a number of components (e.g., lenses, mirrors, rotating compensators, rotating analyzers, processors, etc.) by which the reflected polarized source beam is measured and processed. The detection system 140 is described in greater detail below. Many variants on ellipsometers exist and can be employed to carry out the present invention.

Figure 2:
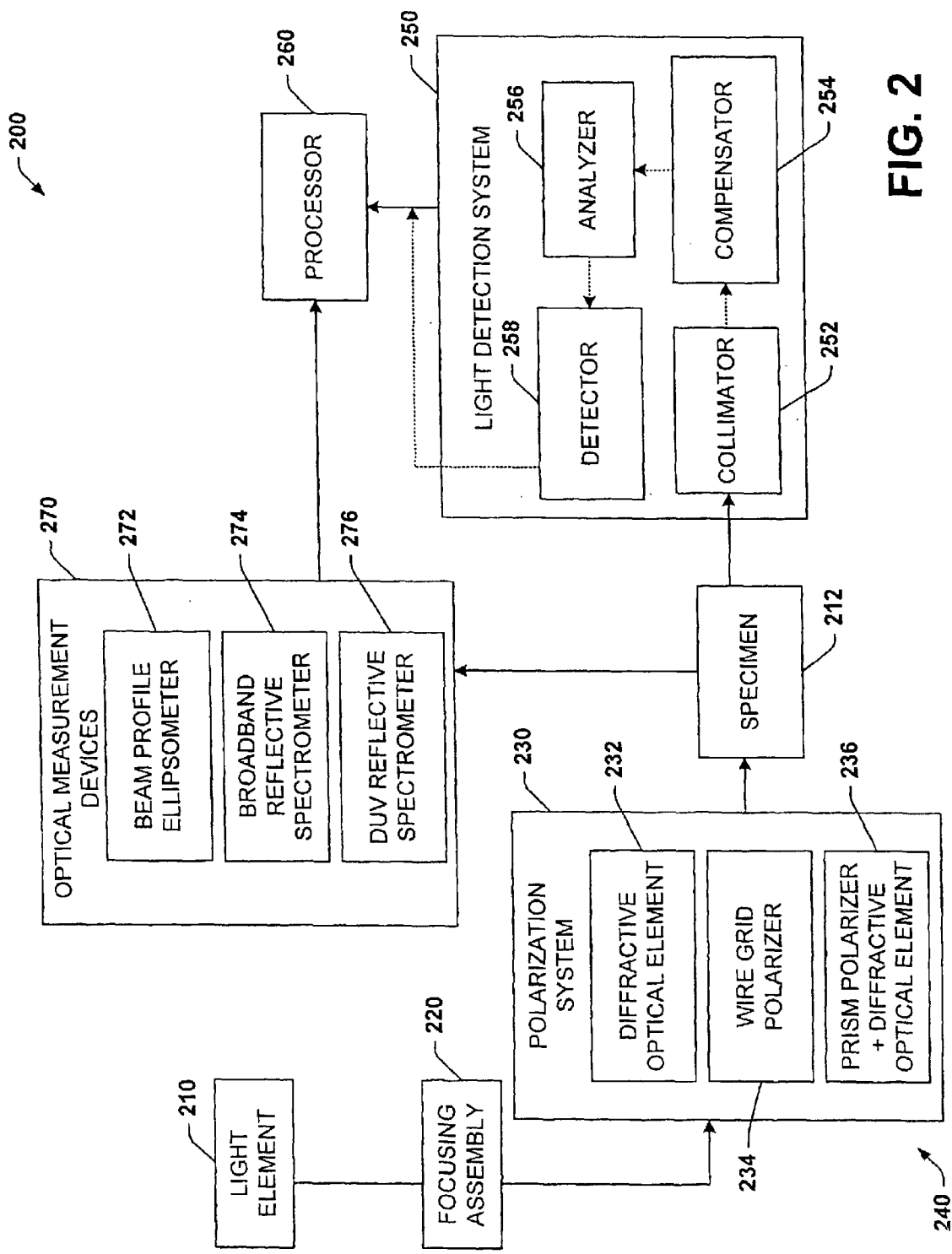
FIG. 2 illustrates a schematic block diagram of a polarization system employed in an optical measurement apparatus in accordance with one aspect of the present invention.

FIG. 2 illustrates a schematic block diagram of an optical measurement system 200 according to another aspect of the present invention. In particular, the system 200 includes a light source 210 which may be a single light source or may be composed of one or more light sources. Examples of suitable light sources include a laser source and a broadband light source. The laser source may produce a pre-set wavelength beam whereas the broadband light source may produce a beam covering a spectrum of about 140 nm to about 900 nm.

The source beam is focused by focusing assembly 220 and then subsequently passed through a polarization system 230 and finally to a specimen 212. The specimen 212 comprises at least a substrate, wherein the composition of the specimen 212 may be only partially known. The polarization system 230 includes at least one of a diffractive optical element 232, a wire grid polarizer 234, and a prism polarizer with an associated corrective diffractive optical element 236. Several configurations of the polarization system 230 may be arranged in order to carry out the present invention. Examples of such configurations are discussed later in FIGS. 3–6.

As can be seen in FIG. 2, the polarization system 230 is located between the focusing assembly 220 and the specimen 212. Such placement of the polarization system 230 facilitates obtaining a well-defined polarization state of the focused source beam of broadband light. Therefore, changes in the properties of focusing element 220 will not change the polarization state of the focused source beam at specimen 212. Further, the well-defined polarization state of the source beam results in a well-defined polarization state of the beam reflected off specimen 212 towards light detection system 250. The specimen properties are therefore more accurately determined, because they are derived from the difference between the polarization states before and after interaction with the specimen.

The polarized focused source beam is transmitted to the specimen 212 and reflected therefrom to a light detection system 250. The light detection system 250 facilitates determining the change in polarization state of the reflected source beam. The light detection system 250 can include a collimator 252, a compensator 254, an analyzer 256 and a detector 258. Element 252 collimates the reflected source beam and directs the reflected source beam to the compensator 254, by which a relative phase delay is introduced. Analyzer 256 extracts a particular polarization state from the light transmitted through compensator 252 and transmits the light of that polarization state to a detector, where the intensities of the different wavelengths of the light beam reaching the detector are measured simultaneously.

The results from the detector 258 are supplied to the processor 260. The processor 260 formulates the intensity information to sets of values. Such values provide information relating to the composition of the specimen 212, particularly when the composition is only partially known as well as optical properties of the specimen 212.

In addition to the spectroscopic ellipsometer 240, other optical measurement devices 270 may be employed either independently of or in combination with the SE in order to evaluate the specimen 212. Other such optical devices 270 include a beam profile ellipsometer 272, a broadband reflective spectrometer 274, and a DUV reflective spectrometer 276. Other measurement devices which could be incorporated but are not illustrated include a vacuum ultraviolet reflective spectrometer, a beam profile reflectometer, and an absolute ellipsometer. See, for example, U.S. Pat. No. 6,278,519, incorporated herein by reference.

The polarization system can be part of an enhanced broadband spectroscopic ellipsometry (BSE) system as discussed in U.S. Pat. No. 5,900,939, entitled THIN FILM OPTICAL MEASUREMENT SYSTEM AND METHOD WITH CALIBRATING ELLIPSOMETER, filed on June 17, 1998, which is commonly owned by the present assignee and the entirety of which is incorporated herein by reference.

Figure 3:
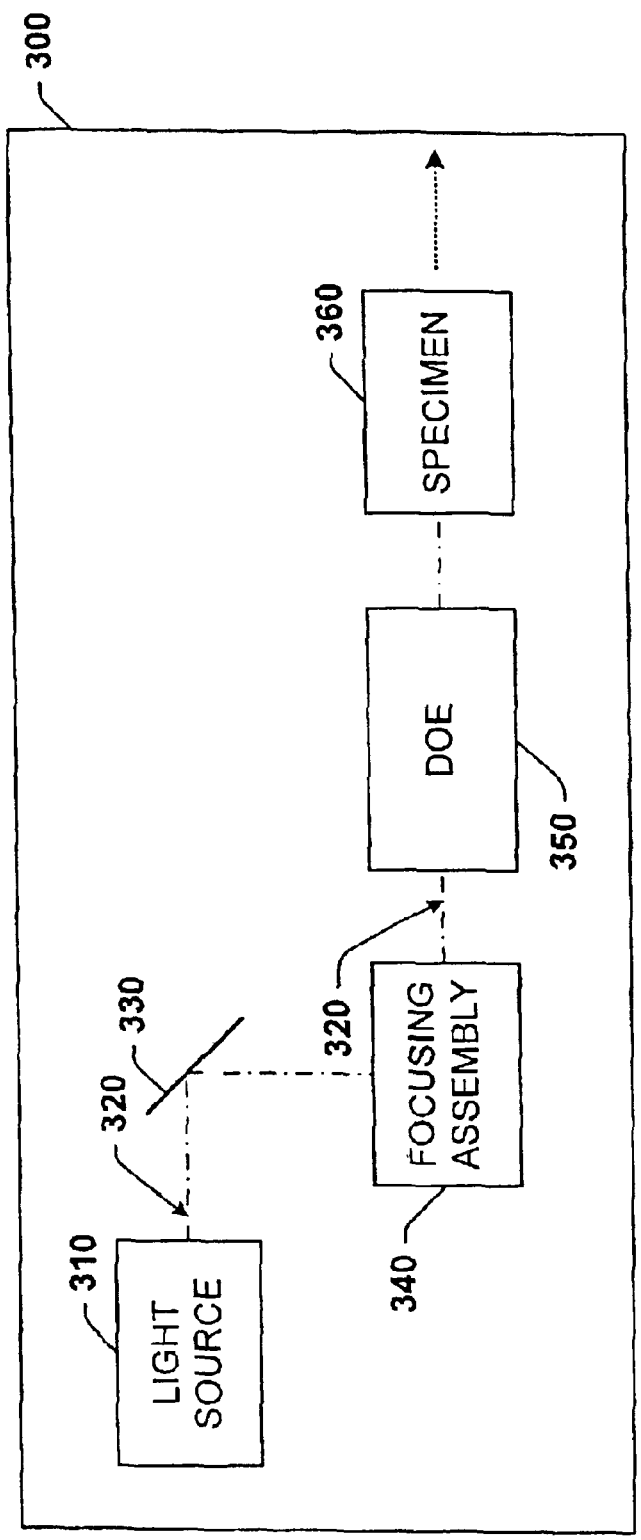
FIG. 3 illustrates a schematic block diagram of a partially constructed optical measurement system in accordance with one aspect of the present invention.

Turning now to FIG. 3, a partial plan view of a SE configuration 300 according to one aspect of the present invention is schematically illustrated. The SE configuration 300 includes a light source 310 for directing a source beam 320 of broadband light to a mirror 330. The mirror 330 passes the source beam 320 to a focusing assembly 340, which focuses the source beam to a diffractive optical element 350.

The diffractive optical element 350 polarizes the source beam 320 after it has been focused. Subsequently, the polarized source beam 320 is transmitted to a surface of a specimen 360. In particular, the polarized source beam 320 is focused to a source spot on the specimen 360. The source beam 320 is reflected from the specimen 360 to light detecting components (not shown) where changes in the polarization state of the light at various wavelengths can be measured, analyzed and computed to assist in evaluating the specimen 360.

One or more diffractive optical elements may be arranged in a sequence or assembled together and are employed to polarize the source beam into two separate orthogonally polarized beams. These two beams are focused to different locations (e.g., source spots) on the specimen.

For example, one polarization state has maximum diffraction efficiency in one order, and the other orthogonal polarization state has maximum efficiency in a different order. Use of the diffractive optical element facilitates spatial filtering, for example, at the entrance aperture of a spectrometer (not shown; discussed in FIG. 2), such that only the desired polarization state is allowed to pass through to the detector. Furthermore, the polarization efficiency can be optimized by generating a phase grating (not shown) on the focusing mirror or lens. Alternatively, or in addition, multiple diffractive optical elements may be employed in order to increase the degree of polarization.

Figure 4:
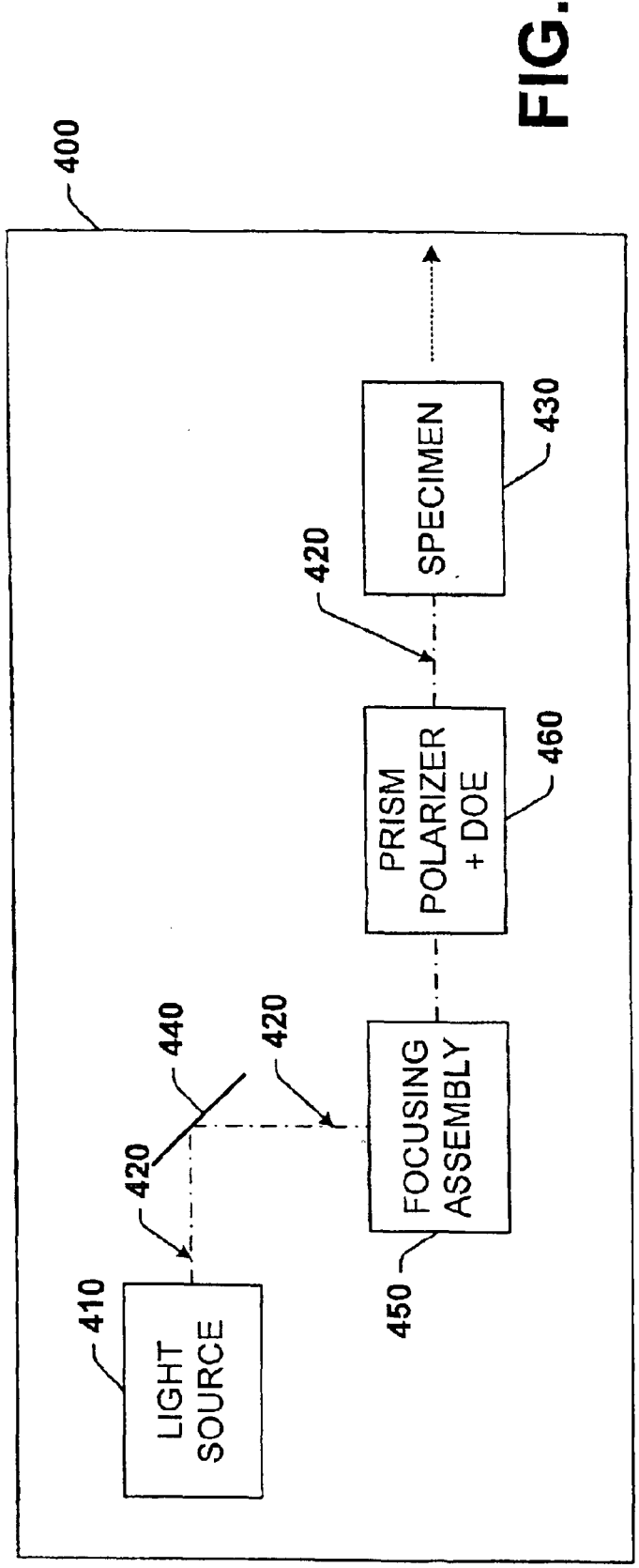
FIG. 4 illustrates a schematic block diagram of a partially constructed optical measurement system in accordance with one aspect of the present invention.

FIG. 4 schematically represents a partial plan view of a SE configuration 400 according to another aspect of the present invention. The SE configuration 400 provides a light source 410 for directing at least part of a source beam 420 of broadband light through a series of components to ultimately reach a specimen 430. More specifically, the source beam 420 is directed to a focusing assembly 450 by a mirror 440. The focusing assembly 450 focuses the source beam 420 through a polarization system 460 to the specimen 430. The polarization system 460 includes a prism polarizer and one or more diffractive optical elements attached or added to one or more surfaces of the prism polarizer. Employing the diffractive optical element with the prism polarizer reduces aberrations in the focused beam. As a result, the size of the source spot on the specimen can be minimized as desired.

Figure 5:
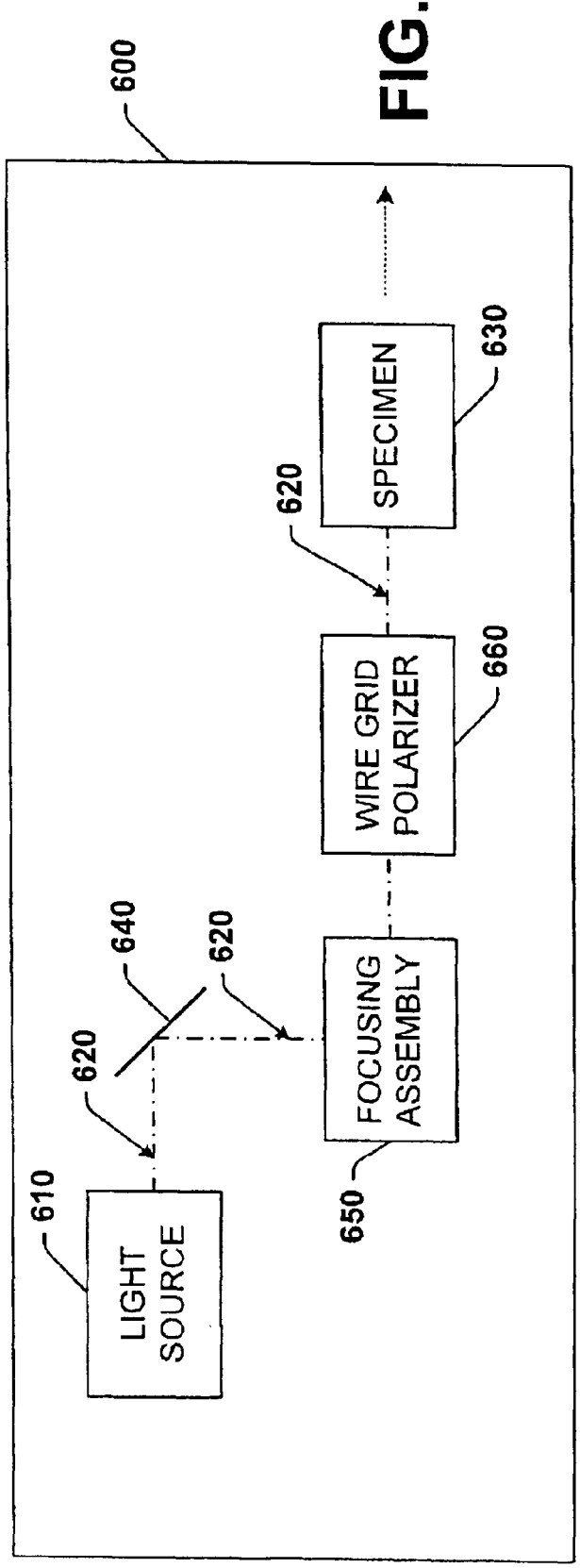
FIG. 5 illustrates a schematic block diagram of a partially constructed optical measurement system in accordance with one aspect of the present invention.

FIG. 5 displays a partial plan view of a SE configuration 600 for obtaining increased throughput from a focused beam in a SE according to still another aspect of the present invention. The SE configuration 600 includes a light source 610 for providing a source beam 620 that is to be focused onto a surface of a specimen 630. The source beam 620 is directed to a focusing assembly 650 by a mirror 640. The focusing assembly 650 focuses the source beam 620 through a wire grid polarizer 660, where the source beam 620 is essentially polarized such that one polarization state of the source beam is then transmitted to the surface of the specimen 630. The wire grid polarizer 660 operates as a broadband dichroic sheet polarizer in the focused source beam 620 of the SE. The wire grid polarizer 660 polarizes the source beam 620 after it has been reflected from the focusing mirror—and not prior as is done in a conventional SE device.

According to one aspect of the present invention, the wire grid polarizer 660 permits one linear polarization state to be transmitted forward to the specimen 630 while the orthogonal polarization state is either reflected or absorbed. This may be accomplished in part by using a grid spacing that is smaller than the shortest wavelength of the source beam 620. When dealing with broadband light, the grid spacing is tailored to optimize the polarization of the shortest wavelengths as longer wavelengths are generally more efficiently polarized by a wire grid.

Furthermore, the effective medium combination of wire and adjacent areas is linearly dichroic. Therefore, not more than one linear polarization state is transmitted to the specimen 630.

In addition, the wire grid polarizer comprises a substrate having a material such with a high transmittance in the spectral range that is to be detected. For example, $CaF_2$, LiF, $MgF_2$, $BaF_2$ and $Al_2O_3$ are suitable materials particularly when the SE is operating in a vacuum ultraviolet to infrared spectral range. Furthermore, the material of the wire grid polarizer substrate may be isotropic and/or anisotropic. With respect to the anisotropic materials, it should be appreciated that the optical axes of the anisotropic material are sufficiently oriented with respect to the wire grid.

Figure 6:
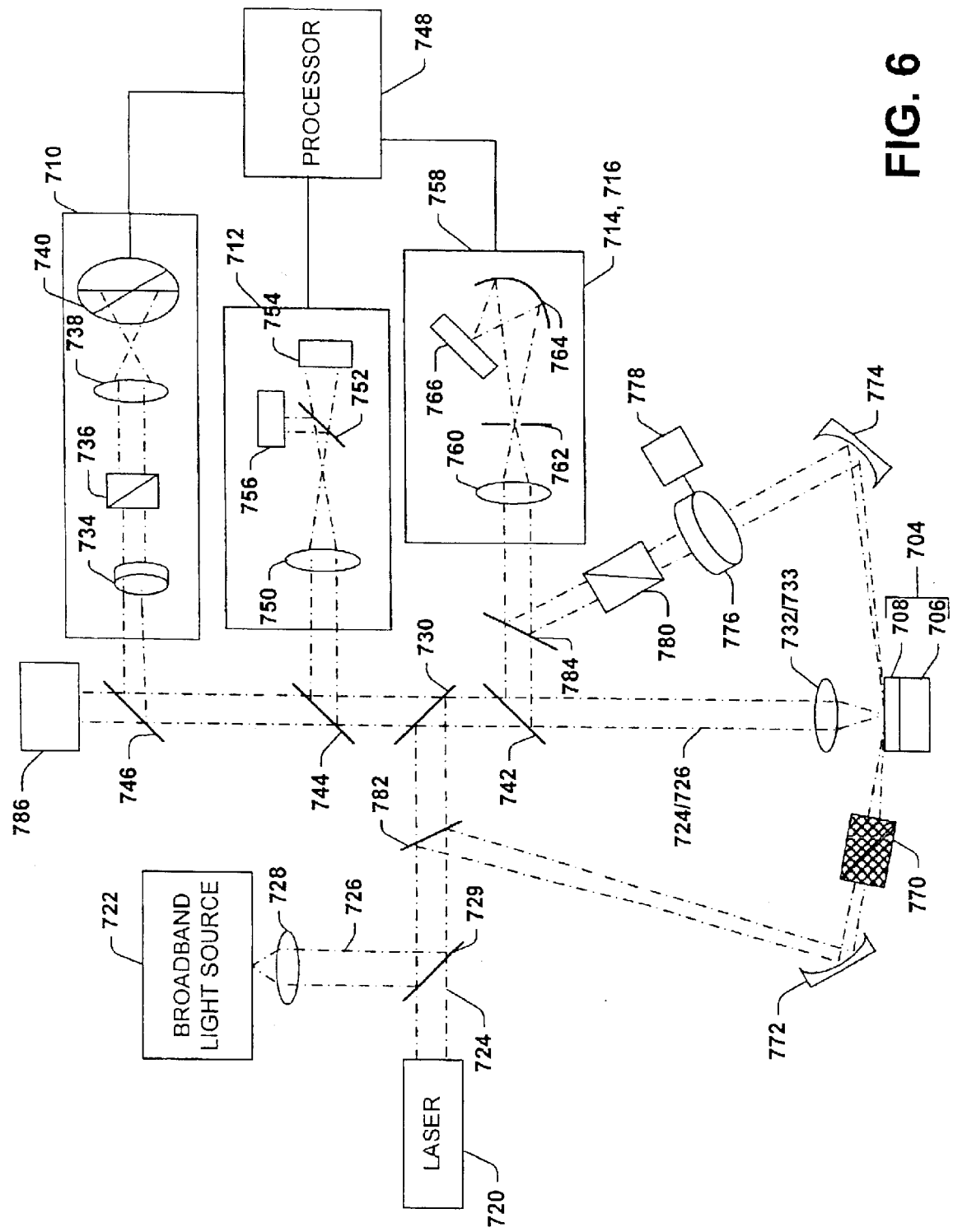
FIG. 6 is a plan view of a composite optical measurement system with a polarization system in accordance with another aspect of the present invention.

Turning now to FIG. 6, a composite optical measurement system 700 for mitigating errors in the analysis of SE data according to the present invention is illustrated. The system 700 includes a Beam Profile Ellipsometer (BPE) 710, a Beam Profile Reflectometer (BPR) 712, a Broadband Reflective Spectrometer (BRS) 714, a Deep Ultra Violet Reflective Spectrometer (DUV) 716, and a Broadband Spectroscopic Ellipsometer (BSE) 718. These five optical measurement devices utilize as few as two optical sources: laser 720 and one or more broadband light sources 722 such as tungsten, xenon, and deuterium bulbs. Laser 720 generates a source beam 724, and broadband light source 722 generates source beam 726 (which is collimated by element 728 and directed along the same path as source beam 724 by mirror 729). Laser 720 may be a solid state laser diode from which emits a linearly polarized beam. Broadband light source 722 can be, for example, a deuterium-tungsten or Xenon lamp that produces a polychromatic probe beam. The source beams 724/726 are reflected by mirror 730, and pass through mirror 742 to specimen 704.

The source beams 724/26 are focused onto the surface of the specimen with a lens 732 or lens 733. Lens 732 is a microscope objective lens with a high numerical aperture (on the order of 0.90 NA) to create a large spread of angles of incidence with respect to the specimen surface, and to create a spot size of about one micron in diameter. Lens 733 is a reflective lens having a lower numerical aperture (on the order of 0.4 NA) and capable of focusing deep UV light to a spot size of about 10 microns to 15 microns.

BPE 710 includes a quarter wave plate 734, polarizer 736, lens 738 and a quad detector 740. In operation, linearly polarized source beam 724 is focused onto specimen 704 by lens 732. Light reflected from the specimen 704 surface passes up through lens 732, through mirrors 742, 730 and 744, and is directed into BPE 710 by mirror 746. The positions of the rays within the reflected source beam correspond to specific angles of incidence with respect to the specimen's surface. Quarter-wave plate 734 retards the phase of one of the two linear polarization state components of the beam by 90 degrees.

Linear polarizer 736 transmits a linear polarization state component of the beam along a path that reaches the detector. For maximum signal, the axis of the polarizer 736 is oriented at an angle of about 45 degrees with respect to the fast and slow axis of the quarter-wave plate 734. Detector 740 is a quad-cell detector with four radially disposed quadrants that each intercept one quarter of the source beam and generate a separate output signal proportional to the power of the portion of the source beam striking that quadrant. The output signals from each quadrant are sent to a processor 748. The processor 748 performs various calculations to generate ellipsometric data relating to the specimen 704.

Beam profile reflectometry (BPR) 712 includes a lens 750, beam splitter 752 and two linear detector arrays 754 and 756 to measure the reflectance of the specimen. In operation, linearly polarized source beam 724 is focused onto specimen 704 by lens 732, with various rays within the beam striking the specimen surface at a range of angles of incidence. Light reflected from the specimen surface passes up through lens 732, through mirrors 742 and 730, and directed into BPR 712 by mirror 744. The positions of the rays within the reflected source beam correspond to specific angles of incidence with respect to the specimen's surface. Lens 750 spatially spreads the beam two-dimensionally.

Beam splitter 752 separates the S and P components of the beam, and detector arrays 754 and 756 are oriented orthogonal to each other to isolate information about S and P polarized light. The higher angles of incidence rays will fall closer to the opposed ends of the arrays. The output from each element in the diode arrays will correspond to different angles of incidence. Detector arrays 754/756 measure the intensity across the reflected source beam as a function of the angle of incidence with respect to the specimen surface. The processor 748 receives the output of the detector arrays 754/756, and derives the thickness and refractive index of the thin film layer 708 based on these angular dependent intensity measurements by utilizing various types of modeling algorithms. Optimization routines which use iterative processes such as least square fitting routines are typically employed.

Broadband reflective spectrometer (BRS) 714 simultaneously probes the specimen 704 with multiple wavelengths of light. BRS 714 uses lens 732 and includes a broadband spectrometer 758 which can be of any type commonly known. The spectrometer 758 shown in FIG. 6 includes a lens 760, aperture 762, dispersive element 764 and detector array 766. During operation, source beam 726 from broadband light source 722 is focused onto specimen 704 by lens 732. Light reflected from the surface of the specimen passes up through lens 732, and is directed by mirror 742 (through mirror 784) to spectrometer 758. The lens 760 focuses the source beam through aperture 762, which defines a spot in the field of view on the specimen surface to analyze. Dispersive element 764, such as a diffraction grating, prism or holographic plate, angularly disperses the beam as a function of wavelength to individual detector elements contained in the detector array 766. The different detector elements measure the optical intensities of the different wavelengths of light contained in the source beam, preferably simultaneously.

Alternatively, detector 766 can be a CCD camera, or a photomultiplier with suitably dispersive or otherwise wavelength selective optics. It should be appreciated that a monochrometer could be used to measure the different wavelengths serially (one wavelength at a time) using a single detector element. Further, dispersive element 764 can also be configured to disperse the light as a function of wavelength in one direction, and as a function of the angle of incidence with respect to the specimen surface in an orthogonal direction, so that simultaneous measurements as a function of both wavelength and angle of incidence are possible. Processor 748 processes the intensity information measured by the detector array 766.

Deep ultra violet reflective spectrometry (DUV) 716 simultaneously probes the specimen with multiple wavelengths of ultra-violet light. DUV 716 uses the same spectrometer 758 to analyze source beam 726 as BRS 714, except that DUV 716 uses the reflective lens 733 instead of focusing lens 732. To operate DUV 716, a turret containing lenses 732 1733 is rotated so that reflective lens 733 is aligned in source beam 726. Alternatively, there may be a separate lens exchanger for each lens 732 and 733 such that one of the lenses is moved out of source beam 726 and then the other lens is aligned in source beam 726. The reflective lens 733 is necessary because refractive objective lenses cannot sufficiently focus the UV light onto the specimen.

Broadband spectroscopic ellipsometry (BSE) includes a polarization system 770, focusing mirror (or lens assembly) 772, collimating mirror 774, rotating compensator 776, and analyzer 780. In operation, mirror 782 directs at least part of source beam 726 to a focusing element 772. Focusing element 772 focuses the beam through the polarization system 770 and then onto the specimen surface at an oblique angle, for example, on the order of 70 degrees to the normal of the specimen surface. The polarization system 770 comprises at least one of a diffractive optical element, a grid wire polarizer or a prism polarizer in combination with a diffractive optical element. As a result, a single polarization state is transmitted to the specimen.

The reflected beam is collimated by mirror 774, which directs the beam to the rotating compensator 776. Compensator 776 introduces a relative phase delay (phase retardation) between a pair of mutually orthogonal polarized optical beam components. Compensator 708 is rotated at an angular velocity about an axis substantially parallel to the propagation direction of the beam, preferably by an electric motor 778. Analyzer 780, preferably another linear polarizer, transmits a linear polarization state component of the beam to the detector. By measuring the light transmitted by analyzer 780, the polarization state of the reflected source beam can be determined. Mirror 784 directs the beam to spectrometer 758, which simultaneously measures the intensities of the different wavelengths of light in the reflected source beam that pass through the compensator/analyzer combination and on to the detector. Processor 748 receives the output of the detector 766, and processes the intensity information measured by the detector 766 as a function of wavelength and as a function of the azimuth (rotational) angle of the compensator 776 about its axis of rotation. Detector/camera 786 is positioned above mirror 746, and can be used to view reflected beams off of the specimen 704 for alignment and focus purposes.

The BPE 710, BPR 712, BRS 714, DUV 716, and BSE 718 may also be calibrated as discussed in U.S. Pat. No. 5,900,939, the entirety of which has been incorporated herein by reference.

Because the BSE 718 polarizes the source beam after it has been reflected from the focusing assembly, complications and errors arising in the analysis of the SE data are mitigated, if not eliminated. It should be appreciated that a focusing lens or lens assembly may be used in place of the focusing mirror 772.

Although the invention has been shown and described with respect to various aspects, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. An optical measurement system comprising a spectroscopic ellipsometer for evaluating characteristics of a specimen, the spectroscopic ellipsometer comprising:

a broad band light source for generating a polychromatic probe beam;

an optical element for focusing the probe beam;

a polarization system comprising at least one diffractive optical element, wherein the polarization system is located between the focusing element and the specimen such that the probe beam is polarized after being focused; and a light detection system for determining the change in polarization state of the probe beam after reflection from the specimen.

2. An optical measurement system comprising a spectroscopic ellipsometer for evaluating characteristics of a specimen, the spectroscopic ellipsometer comprising:

a broad band light source for generating a polychromatic probe beam;

an optical element for focusing the probe beam;

a polarization system comprising at least one wire grid polarizer wherein the polarization system is located between the focusing element and the specimen such that the probe beam is polarized after being focused; and a light detection system for determining the change in polarization state of the probe beam after reflection from the specimen.

3. The system of claim 1 or 2, wherein the probe beam comprises a plurality of wavelengths of broadband light including both visible and UV wavelengths.

4. The system of claim 1 or 2, wherein the focusing element comprises any one of a mirror or lens.

5. The system of claim 1, wherein the polarization system further comprises a prism polarizer such that the at least one diffractive optical element is added to one or more surfaces of the prism polarizer to compensate for aberrations introduced into the source beam by the prism polarizer.

6. The system of claim 2, wherein the wire grid polarizer has a grid spacing smaller than the shortest measured wavelength.

7. The system of claim 2, wherein the material forming the wire grid is selected from the group consisting of $CaF_2$, $LiF$, $MgF_2$, $SiO_2$, $BaF2$ and $Al_2O_3$, and any combination thereof.

8. The system of claim 1, wherein the diffractive optical element comprises a substrate material, the substrate material having a surface shape, wherein aberrations occurring on the substrate surface are mitigated by employing a binary phase grating on one or more of the substrate surfaces.

9. The system of claim 1 or 2, wherein the probe beam is focused onto the surface of the specimen to a spot size less than 50 microns in diameter.

10. The system of claim 1 or 2, wherein the probe beam is focused onto the surface of the specimen to a spot size less than 25 microns in diameter.

11. An optical measurement system comprising a spectroscopic ellipsometer for evaluating characteristics of a specimen, the spectroscopic ellipsometer comprising:

a broad band light source for generating a polychromatic probe beam;

an optical element for focusing the probe beam;

a polarization system comprising at least one diffractive optical element, wherein the polarization system is located between the focusing element and the specimen such that the probe beam is polarized into two orthogonal polarization states after being focused; and a light detection system positioned to receive a desired polarization state from said two orthogonal polarization states and determine the change in the desired polarization state after reflection from the specimen.

12. An optical measurement system comprising a spectroscopic ellipsometer for evaluating characteristics of a specimen, the spectroscopic ellipsometer comprising:

a broad band light source for generating a polychromatic probe beam;

an optical element for focusing the probe beam;

a polarization system comprising at least one wire grid polarizer, wherein the polarization system is located between the focusing element and the specimen such that a single polarization of the probe beam is transmitted after being focused; and a light detection system for determining the change in the single polarization state of the probe beam after reflection from the specimen.

* * * * *